US00PP08506P

United States Patent [19]

Marciel et al.

[11] Patent Number: Plant 8,506

[45] Date of Patent: Dec. 21, 1993

[54] HYBRID TEA ROSE PLANT NAMED DEVMOMENTO

[75] Inventors: Stanley G. Marciel; Jeanne A. Marciel, both of Aptos, Calif.

[73] Assignee: DeVor Nurseries, Inc., Watsonville, Calif.

[21] Appl. No.: 974,118

[22] Filed: Nov. 10, 1992

[51] Int. Cl.[5] ..... A01H 5/00

[52] U.S. Cl. ..... Plt./15

[58] Field of Search ..... Plt./11, 15

*Primary Examiner*—Howard J. Locker

*Attorney, Agent, or Firm*—Christie, Parker & Hale

[57] ABSTRACT

A new hybrid tea rose plant producing yellow flowers.

1 Drawing Sheet

SUMMARY OF THE INVENTION

The present invention relates to a new and distinct variety of rose plant of the hybrid tea rose class which was originated by my crossing as seed parent the variety known as 'Capella' and as pollen parent an unnamed and unpatented seedling of my creation. The varietal denomination of this new rose is Devmomento'.

Among the novel characteristics possessed by this new variety which distinguish it from its parents and all other varieties of which I am aware are its attractive well formed golden yellow flowers borne on a plant particularly suitable for use for cut-flower production in greenhouses. Flowers, which are borne on nearly thornless stems, remain attractive through all stages, and color remains very stable.

Blooms of 'Devmomento' are much larger than blooms of its parent 'Capella' and have a deeper golden color. The stem length of the new variety is obtained from the male parent, which was an orange-flowered seedling.

Asexual reproduction by budding of the new variety as performed in Watsonville, Calif. shows that the foregoing and other distinguishing characteristics come true to form and are established and transmitted through succeeding propagations.

BRIEF DESCRIPTION OF ILLUSTRATIONS

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

Parentage: Seedling.

*Seed parent.*—'Capella'.

*Pollen parent.*—Unnamed seedling (81191-2).

Class: Hybrid tea.

The following is a detailed description of my new variety, of new specimens grown under glass in Watsonville, Calif. in the month of September. The color terminology used is in accordance with The Royal Horticultural Society Colour Chart (RHSCC), and refers to plate numbers in the aforementioned color chart. Phenotypic expression may vary depending on light and cultural conditions.

FLOWER

Blooming habit: Continuous.

A. Bud:

(1) *Size.*—Medium.

(2) *Form.*—Pointed and tapering.

(3) *Color.*—As sepals divide, bud color is near 10A.

(4) *Sepals.*—Upright and close to bud, then spreading and reflexing; some sepals are foliaceous. Color: Near 144A on outside.

(5) *Peduncle.*—Length: About 14 cm to 17 cm. Aspect: Straight. Strength: Erect, sturdy. Color: Near 144A.

(6) *Bracts.*—Generally not present.

B. Bloom:

(1) *Size.*—Average size when fully expanded — about 9 to 10 cm.

(2) *Borne.*—Singly, one to a stem.

(3) *Form.*—Imbricated with reflexed petals; blooms open fully to reveal center.

(4) *Petalage.*—Number of petals under normal conditions — about 22 to 28.

(5) *Color.*—After sepals fall and petals unfurl, predominant flower color viewing top surface of outer petals at ⅓ to ½ open is near 8A to near 7B toward petal base. Undersurface of outer petals is near 10B to near 9B toward base. Top surface of inner petals is near 12B with near 9A toward base. Undersurface is near 12C with near 9B toward base. Color at point of petal attachment is near 9A. Top surface of outer petals of fully open blooms is near 9D with near 12C toward base and near 14A at point of petal attachment. Undersurface is near 9D with near 10B toward base and near 12B at point of attachment. Top surface of inner petals is near 10D with near 10A toward base and near 14A at point of attachment. Undersurface is near 10C with near 10B toward base and near 12A to 12B at point of attachment. Color of bloom upon aging lightens a little toward near 9D (petal top surface) to near 10C (petal undersurface).

C. Petals:

(1) *Texture.*—Thick.

(2) *Appearance.*—Inside and outside are smooth with a matte finish.

(3) *Form.*—Smooth, slightly ruffled.

(4) *Arrangement.*—Regularly arranged, imbricated.

(5) *Petaloids.*—Few.

(6) *Fragrance.*—Slight musk.

(7) *Lasting quality.*—6 to 7 days on plant and as cut flower.

REPRODUCTIVE ORGANS

A. Stamens:
(1) *Arrangement.*—Not regularly arranged.
(2) *Anthers.*—Color — near 22A.
(3) *Filaments.*—Color — near 9B.
(4) *Pollen.*—Color — near 22A.

B. Pistils:
(1) *Styles.*—Bunched, medium length, thin.
(2) *Stigmas.*—Color — near 1D.

C. Characteristics of hips: Round but depressed at top; near 163A; about 3.5 cm wide, 3 cm long; seeds do not protrude.

PLANT

A. Form: Upright.

B. Growth: Vigorous, uniform branching; height attained about 254 cm at first season.

C. Foliage: Compound 3, 5 and 7 leaflets.
(1) *Size.*—Medium.
(2) *Quantity.*—Abundant.
(3) *Color.*—Upper side — near 147A. Under side — near 147B.
(4) *Shape.*—Oval.
(5) *Texture.*—Leathery, smooth.
(6) *Edge.*—Serrate.
(7) *Serration.*—Denticulate.
(8) *Leaf stem.*—Color — medium green.

(9) *Stipules.*—Medium length, adnate, tipped with tiny glands.
(10) *Rachis.*—Small prickles.
(11) *Petioles.*—Top — near 166A along edges with near 146B inside; underside near 146B.
(12) *Auricle.*—Slender and triangular.
(13) *Resistance to disease.*—Under greenhouse conditions no rust and black spot; good resistance to mildew.

D. Wood:
(1) *New wood.*—Color — near 146A. Bark — smooth.
(2) *Old wood.*—Color — near 146B. Bark — smooth.

E. Flower stem: About 46 to 52 cm from last cut.

F. Thorns:
*Quantity (main stalk).*—Ordinary.
*On laterals from stalk.*—Very few.
*Form.*—Thin, straight.
*Length.*—Variable.
*Color.*—Near 144C when young.
*Position.*—Irregular.
*Prickles.*—Profuse.

G. Winter hardiness: Greenhouse variety; wintered well in California.

I claim:

1. A new and distinct variety of rose plant of the hybrid tea rose class, substantially as shown and described.

* * * * *

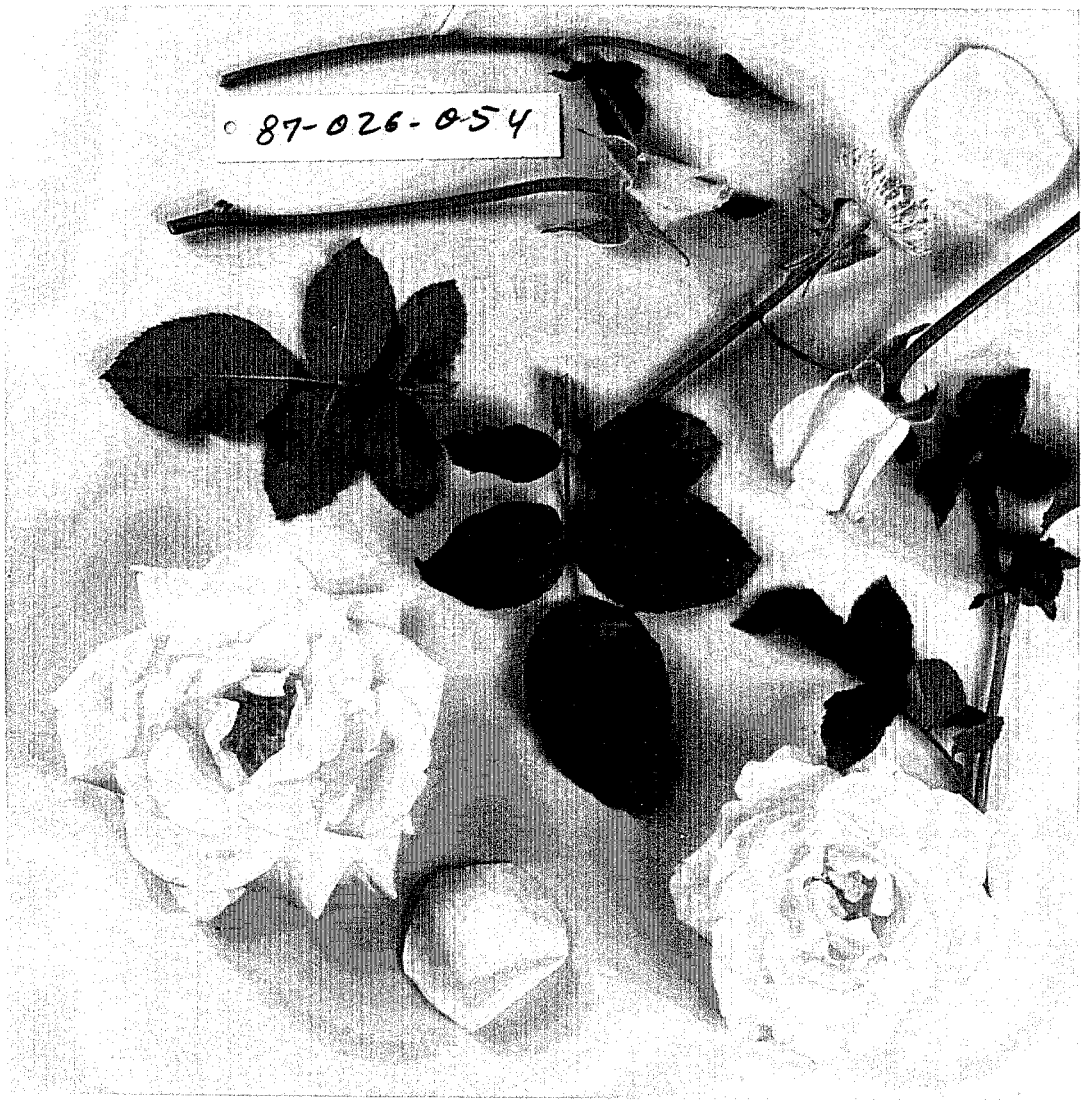
87-026-054